Figure 1:

United States Patent [19]

Neumiller

[11] Patent Number: 5,145,604
[45] Date of Patent: * Sep. 8, 1992

[54] AQUEOUS EMULSION AND AEROSOL DELIVERY SYSTEM USING SAME

[75] Inventor: Phillip J. Neumiller, Racine, Wis.

[73] Assignee: S. C. Johnson & Son, Inc., Racine, Wis.

[*] Notice: The portion of the term of this patent subsequent to Feb. 25, 2009 has been disclaimed.

[21] Appl. No.: 832,168

[22] Filed: Feb. 6, 1992

Related U.S. Application Data

[63] Continuation-in-part of Ser. No. 584,963, Sep. 19, 1990, Pat. No. 5,091,111.

[51] Int. Cl.$^5$ .................. C09K 3/00; B01J 13/00
[52] U.S. Cl. .................. 252/312; 252/365; 252/314; 252/351; 424/450; 428/402.2; 514/938
[58] Field of Search ........... 252/311, 312, 305, 351, 252/314; 428/402.2; 514/938; 424/450

[56] References Cited

U.S. PATENT DOCUMENTS

| | | | |
|---|---|---|---|
| 4,439,342 | 3/1984 | Albanese | 252/305 |
| 4,439,343 | 5/1984 | Albanese | 252/305 |
| 4,536,323 | 8/1985 | Stopper | 252/305 |
| 4,536,324 | 8/1985 | Fujiwara et al. | 252/311 |
| 4,655,959 | 4/1987 | Stopper | 252/305 |
| 4,772,471 | 9/1988 | Vanlerberghe et al. | 424/450 |
| 4,860,685 | 9/1989 | Smith | 118/300 |
| 4,861,580 | 8/1989 | Janoff et al. | 424/1.1 |
| 4,885,159 | 12/1989 | Miyake et al. | 424/70 |
| 4,911,928 | 3/1990 | Wallach | 424/450 |
| 4,917,765 | 4/1990 | Ferguson et al. | 162/168.2 |
| 4,917,951 | 4/1990 | Wallach | 428/402.2 |
| 5,013,557 | 5/1991 | Tai | 424/493 |
| 5,091,111 | 2/1992 | Neumiller | 252/305 |

FOREIGN PATENT DOCUMENTS

2078543A 1/1982 United Kingdom.
2166107A 4/1986 United Kingdom.

OTHER PUBLICATIONS

Spontaneous Vesicle Formation in Aqueous Mixtures of Single-Tailed Surfactants, by Kaler et al., *Science*, Sep. 22, 1989, p. 1371.

*Primary Examiner*—Richard D. Lovering
*Assistant Examiner*—N. Bhat

[57] ABSTRACT

An aqueous emulsion system containing vesicular structures which provides a delivery system for a variety of active ingredients. The vesicular structures of the emulsion provide a reservoiring or slow-release effect for the active ingredient or for a propellant, enabling an aerosol delivery system to be effective with a very low VOC content.

31 Claims, 4 Drawing Sheets

⊢――――⊣ 1 μm
⊢―⊣ 100 nm

⊢⎯⎯⎯⎯⎯⎯⊣ 1 μm
⊢⎯⊣ 100 nm

FIG. 4

Bar chart showing Protection Time (Hours) for Vesicular DEET vs DEET Solution across M LANDS, SF LANDS, M BITES, SF BITES.

FIG. 5

Bar chart showing Protection Time (Hours) for Vesicular DEET vs DEET Aerosol across M LANDS, SF LANDS, M BITES, SF BITES.

AQUEOUS EMULSION AND AEROSOL DELIVERY SYSTEM USING SAME

TECHNICAL FIELD

This application is a Continuation-In-Part of Applicant's co-pending application, Ser. No. 07/584,963, filed Sep. 19, 1990. Now U.S. Pat. No. 5,091,111.

This invention relates to the field of aqueous emulsion systems and the use of such systems for dispensing aerosols from pressurized containers and more particularly to an improved emulsion system which contains vesicle structures that can be used to provide a reservoiring effect for the propellant component of an aerosol delivery system.

BACKGROUND ART

A vesicular system may be considered as a particular type of emulsion system, in which the dispersed or emulsified phase particles are layered vesicles which are suspended in the continuous phase.

The fact that vesicular systems can be formed and then used to entrap and carry desirable active compounds is well known. Such systems have most frequently been formed from organic materials of biological origin such as lipids (see, e.g., U.S. Pat. No. 4,772,471), Vitamin E (U.S. Pat. No. 4,861,580), or steroids (U.S. Pat. No. 4,917,951), and have been especially used in the pharmaceutical fields to provide carriers for biologically active materials.

A method of making, from non-phospho-lipid surfactants, paucilamellar vesicles having a central cavity substantially filled with a water-immiscible oily material is disclosed by U.S. Pat. No. 4,911,928 to Wallach, Paucilamellar Lipid Vesicles. The "lipid vesicles" disclosed by this patent are large (500 nm diameter minimum) multilayered liposome-like structures which are centrifuged (at 10,000-14,000 rpm for 15 minutes) out of the system after formation.

The creation of a vesicular dispersion from non-ionic surfactants is disclosed by U.S. Pat. No. 4,536,324 to Fujiwara et al., Nonionic Surfactant Type Vesicle Dispersion, which discloses a vesicle system formed from non-ionic surfactants such as polyoxethylene castor oil ethers or hardened castor oil ethers combined with sorbitan polyesters of long chain fatty acids in water. Conventional mixing means, from mechanical to ultrasonic, are used to form the vesicle dispersion or emulsion. Suggested uses for the dispersion or emulsion are either alone as a cosmetic cream or lotion or for containing a lipophilic or hydrophilic pharmaceutically active component.

The creation of a vesicle system from a mixture of cationic and anionic surfactants in water has been reported by Kaler et al. (Science, Sep. 22, 1989, p. 1371) Gentle mixing of cetyltrimethyl ammonium tosylate and sodium dodecyl benzene resulted in immediate and spontaneous (no mechanical agitation) generation of vesicles having particle sizes between 30 and 80 nm. The vesicles so formed were said to be stable and able to efficiently encapsulate glucose or other solutes.

Many two component systems for the delivery of an aerosol from a pressurized container are known. One component of such a system must be a gaseous propellant. The other component is a liquid component, which contains the active ingredient to be dispersed, may be comprised of various solvents, or may have an aqueous base with added solvents.

Many propellants currently used (since the use of nonflammable chlorinated fluorocarbons is being limited for environmental reasons) are flammable hydrocarbon gases such as propane, butane, and isobutane. Aqueous systems are preferred for use with such propellants, since such a system can limit or even obviate the flammability of the propellant phase.

The use of microemulsions in an aerosol system is known. U.S. Pat. No. 4,655,959, Preparation of Non-Flammable Aerosol Propellant Microemulsion System, and U.S. Pat. No. 4,536,323, Non-Flammable Propellant Microemulsion System, both issued to Stopper, disclose an aerosol system which, when shaken in its container, forms an oil-in-water microemulsion. This microemulsion structure allows the amount of propellant to be increased up to 50% by weight without flammability problems. Stopper's reason for wishing to have a higher level of propellant than the 15% to 25% conventional limit for non-flammability is his desire to be able to disperse the entire contents of the dispenser.

A countervailing consideration to the desire to incorporate a large amount of propellant into an aerosol system for efficiency of delivery is the desire to limit the amount of volatile organic compounds (VOCs) released into the earth's atmosphere. More immediately critical is the need to reduce the amount of VOCs into the home, for there is concern that indoor air pollution may sometimes exceed external air pollution and this is becoming an issue as a potentially health affecting condition. California, for example, is developing maximum VOC concentration regulations for different product categories. The proposed limit for air freshener double phase aerosols is 30%; for insect 15 repellents, it is 65%. Analysis of one of the lowest VOC-containing aerosols currently on the market shows a VOC content of 28%.

An article in Aerosol Age ("CARB/Industry Negotiate Consumer Product Regs.", Jul. 1990, pp. 22–27) has a table showing the differences between the proposed limits and "industry's needs". Industry need for air fresheners and disinfectants are said to be 70%; for dusting aids, 35%; for hair sprays, 80%. The present invention appears to offer a system that can deliver a variety of active ingredients, making it useable for a wide variety of products, with a total VOC content far below the "industry needs".

Which compounds qualify as VOCs will depend on type as well as molecular weight but, in general, organic compounds with fewer than nine carbon atoms are usually considered potential VOCs. Propane, butane, and isobutane are, obviously, VOCs.

Thus a non-flammable aqueous aerosol system that could effectively deliver the container contents with a lower, rather than a higher, level of propellant is highly desirable both for environmental and regulatory reasons. However, prior art has not only not produced such a system but, as in the Stopper patents, even teaches away from such a possibility.

All aerosol systems require a certain minimum propellant head space pressure to expel the contents of the container. Propellant head space pressure is dependent upon the interaction the propellant has with other substances in the container.

A container charged with propane alone (no other substances in the container) will exhibit a head space pressure of 100–110 psi (7031 gr/sq. cm–7734.1 gr/sq.cm). A container containing water that is then filled with propane will exhibit a head space pressure of 110–120 psi (7834.1 gr/sq. cm–8437.2 gr/sq. cm). When alcohol, glycerol, or a surfactant is added to the water, the head space pressure can be lowered. A mixture of 66% water, 30% ethanol, and 4% propane will exhibit a head space pressure of 50 psi, which is a near optimum head space pressure for an aerosol system which will produce a spray. 55 psi (3867 gr/sq. cm) pressure is considered the optimum figure.

A further consideration for an effective aerosol system is the ability of the system to maintain the desired pressure as the contents and the propellant are expelled. The alcohol-water-propane system described above exhibits progressively decreased head space pressure as the contents are expelled from an aerosol container with a vapor tap valve.

A desirable aerosol system should thus have the capacity to entrap or reservoir some of the propellant phase and progressively release the propellant as the contents of the aerosol container are expelled; thus maintaining a constant-equilibrium head space pressure over most of the usable life of the aerosol container.

SUMMARY DISCLOSURE OF THE INVENTION

The present invention is a unique aqueous emulsion preparation which can be used for delivering an aerosol composition from a pressurized container. It is effective in dispensing the entire contents of the container, yet does so with a lower level of propellant and VOCs than previously possible. Total VOC's of the present invention range from 2% to 25%, compared to the current average aerosol VOC levels of 8% to 98%.

This is accomplished by the production, in the liquid component of the system, of an emulsion preparation that includes discrete vesicular particles which are suspended in a continuous phase and kept in stable suspension by the mixture of surfactant, primary alcohol, and polyhydroxy alcohol or polyhydroxy alcohol ester chosen. The characterization of the discrete particles of the emulsion preparation as vesicles of an average size of 20–100 nm is indicated by photon correlation spectroscopy and confirmed by electron microscopy.

It has been found that such an emulsion preparation can be produced from a combination of non-ionic single- or double-tailed surfactants, primary alcohol, polyhydroxy alcohol or polyhydroxy alcohol ester, and an organic, preferably active, ingredient, and that such a system can entrap or provide a reservoiring effect for small linear organic propellant molecules in the $C_3$–$C_5$ range. The reservoiring effect resulting from increased partitioning of the propellant in these formulations due to enhanced mutual compatibility reduces the amount and/or the rate of loss of propellant into the gas phase when the formulation is exposed to atmospheric pressure by the opening of the vapor tap. This reservoiring effect functions similarly to an increased solubility—more propellant is held within the system and gradually released. This reservoiring equilibrium effect functions to regulate head space pressure within the pressurized container and prevents the decrease of head space pressure that would otherwise occur when a vapor tap valve is used. The fact that the propellant is reservoired within the aqueous phase makes it possible for the system to function properly over the useful life of the aerosol container with a lower concentration of propellant rather than a higher one, which might logically be expected.

BEST MODE FOR CARRYING OUT THE INVENTION

The first step in the preparation of an aqueous aerosol delivery system according to the present invention is the preparation of an aqueous emulsion stage, which is the same as the aqueous component used to produce the aerosol delivery system.

A non-ionic surfactant or a mixture of non-ionic surfactants is mixed with a polyhydroxy alcohol or polyhydroxy alcohol ester and a primary alcohol. A preservative or antimicrobial agent may be added. Then water is added and the mixture homogenized to form a lamellar or liquid crystal phase which is thick (viscosity 20–100 cS), translucent and often exhibits iridescence. An active organic compound, such as a fragrance or an insecticide, is then added to the system. Part of the lamellar liquid crystal structure could be converted into multilamellar liposomes. The degree of this conversion depends mainly on the intensity of shear used in homogenization step. Measured rheological properties such as significant elasticity, shear thinning behavior and high viscosity values at low shear rates indicate that the liquid crystal form is suitable for making shampoos, dermal, and cleaning or polishing formulations.

Next the lamellar stage is subjected to sonification, high energy shearing, or other type of energy addition. This produces a stable aqueous emulsion stage with lower viscosity (approximately 10 cS or lower) which is unclouded and transparent.

Three representative formulations of the invention (one of the lamellar or liquid crystal system and two of the vesicular system) were centrifuged for five hours at 17,000 rpm (102,000 Deg/Sec) at an acceleration of 34,800 g in a Sorvall Superspeed RC2B centrifuge using an SS34 rotor. None of the formulations showed any phase separation. This behavior indicates a very high stability for both the lamellar and the vesicular systems, making them suitable for producing products with long shelf life.

FIGS. 1–3 all show representative TEM photographs selected from over forty sets of photographs from four different formulations. All photographs showed, with expected minor variations, the same structural makeup of the emulsion and vesicular phases of the invention. All samples were rapidly quenched (frozen) to avoid formation of ice crystals. Then the frozen sample was brought to vacuum and fractured. The samples were shadowed with platinum and photographed by TEM. Original TEM photographs were taken as stereo pairs, to be viewed with a stereoscope for maximum resolution.

BRIEF DESCRIPTION OF THE DRAWINGS

FIG. 1, taken at a magnification of 40,300, shows the multilamellar liposome structures contained in a representative preparation of this aqueous emulsion.

FIG. 2, taken at a magnification of 62,000, shows the vesicular structures, which average 20–100 nm in diameter, present in the aqueous emulsion after it has been subjected to sonification.

FIG. 3, taken of a slightly different but also representative formulation of the present invention and taken at a magnification of 46,500 shows that, while the majority of the vesicular structures present in the sonicated aqueous emulsion are between 20 and 100 nm, there are some larger unilamellar vesicular structures present.

FIGS. 4 and 5 are bar graphs showing the results of testing with respect to DEET-containing formulations as described in Example 15 as set forth below. More specifically, FIG. 4 illustrates comparison results with respect to vesicular DEET and DEET solution and FIG. 5 illustrates comparison results with respect to vesicular DEET and DEET aerosol.

According to one aspect of the present invention, the aqueous emulsion stage may be used to form delivery systems for such preparations as polishes, fragrances, pesticides, insect repellents, cleaning products, dermal treatments, etc.

According to a second aspect of the present invention, the aqueous emulsion stage component is next placed into a pressurizable container, which is then charged with a propellant.

The aqueous aerosol delivery system is comprised of the aqueous emulsion stage component, which is present in between 75% to 98% by weight of the system, and a propellant component, present in between 2% to 25% by weight of the system.

The surfactants used to form the aqueous component of the present invention are non-ionic surfactants, which may either be of a single type having double hydrocarbon tails extending from the functional group or be a pair combination of two different types of surfactants having single hydrocarbon tails extending from their functional groups. Mixtures of such types of surfactants may also be used. Possible "double-tailed" non-ionic surfactants which may be used in the system of the present invention are the fatty acid alkanolamides, ethylene oxide adducts of the higher primary alcohols or an ethoxylated amines. Possible "single-tailed" surfactants, which must be used in pairs are sorbitan monooleate, polyoxyethylene (2) oleyl ether, and polyoxyethylene (20) sorbitan monooleate. While it is usually desirable to use either a double-tailed surfactant or a pair combination of single-tailed surfactants, it is also possible to use both a double-tailed surfactant and a single-tailed surfactant combination. Such a combination reduces necessary total level of surfactant as well as providing an opportunity to alter the characteristics of the resulting systems for specific desired features. The surfactants are present in the liquid component in concentrations between 0.25% and 6.5%.

The primary alcohols used to form the aqueous component of the present invention range from ethanol to oleyl alcohol. It appears that a small quantity of a primary alcohol is essential to produce the reservoiring effect which characterizes the invention. It is theorized that this reservoiring effect is produced by the coupling of the propellant into the membranes of the vesicles.

Alcohols below $C_9$, however, are themselves volatile organic compounds, so the preferred alcohols of the present invention are linear $C_9$-$C_{18}$ (nonyl to oleyl) alcohols, with the most preferred alcohols being the $C_{10}$ (decanol) and $C_{11}$ (1-undecanol) alcohols. The primary alcohol is present in the aqueous component in concentrations between 0.001% and 3.5%.

The polyhydroxy alcohol or polyhydroxy alcohol ester used to form the aqueous emulsion stage component of the present invention is preferably a $C_2$-$C_6$ alcohol compound such as glycerol, ethylene glycol, or diethylene glycol. The polyhydroxy alcohol esters are preferably $C_{10}$-$C_{30}$ polyhydroxy alcohol esters. Mixtures of polyhydroxy alcohols and polyhydroxy alcohol esters may be used. Polyhydroxy alcohol ethers may also be useable. The polyhydroxy alcohol or polyhydroxy alcohol ester is present in the aqueous component at concentrations between 0.1% and 6%.

The aqueous component of the present invention may also include a preservative such as methylparaben, present at concentrations between 0.1% and 0.5%.

Included in the aqueous emulsion phase component of the present invention is an organic active ingredient chosen according to the desired characteristics of the final product. Possible organic active ingredients could include fragrances, flavoring agents, pesticides (such as pyrethrin or linalool) or repellents (including personal insect repellents such as N, N-diethylamine-meta-toluamide (DEET)), waxes or other polishing agents (including silicone oils), emollients, cleansers or stain removal agents, etc. The active ingredient may be either lipophilic or hydrophilic. The organic active ingredient is present in the aqueous component at concentrations between 0.01% and 20%.

Water makes up the balance of the aqueous component for all formulations. It is preferred that deionized water be used.

The propellant component of the present invention is a linear chain hydrocarbon, such as propane, butane, pentane or mixtures thereof. The propellant component is, as discussed above, present at concentrations between 2% and 25% by weight of the total system, and preferably between 2% and 10%.

The reservoiring effect of the aerosol system and the need for a long chain alcohol to produce that effect of the present invention is best illustrated by the behavior of the system with two different propellant gases: isobutane and propane. Propane alone exhibits a head space pressure of 110 psi. When a non-ionic surfactant, such as a fatty acid alkanolamide, is added to the container, propane exhibits a pressure of 96 psi (6749.76 gr/sq. cm). When propane is used as the propellant in the system of the present invention prepared without a long chain alcohol, the system has a pressure of 100 psi (7031 gr/sq. cm). When a long chain alcohol is present in the system, propane pressure is 55 psi, (3867 gr/sq. cm) showing the coupling effect of the alcohol in the system with the propellant.

Isobutane alone exhibits a head space pressure of 35 psi (2460.85 gr/sq. cm). When a non-ionic surfactant, such as a fatty acid alkanolamide, is added to the container, the pressure is 32 psi (2249.92 gr/sq. cm). When isobutane is used as the propellant in the system of the present invention (with a long chain primary alcohol present), the system has a pressure of 39 psi (2742 gr/sq. cm). Isobutane thus appears unable to couple into the system even in the presence of a long chain primary alcohol.

It is believed that the reservoiring effect is produced by the penetration into or coupling with the membranes of the vesicular structures of the propellant molecules. Propane (as well as butane and n-pentane) molecules, being sterically slender, fit between the molecules of the membrane. Isobutane, however, being sterically more bulky, is unable to fit completely into the vesicular structure in this manner.

Combinations of non-ionic surfactants, primary alcohols, and polyhydroxy alcohols or polyhydroxy alcohol esters that have been tested and have produced stable aerosol systems use components selected from the following groups:

PREFERRED SURFACTANTS

Single Surfactants (% concentration range 0.25–6.5)

Fatty acid alkanolamide (Monamid 150 ADY)
Linoleamide (Monamid B-442)
Tallow monoethanolamide ethoxylate (Sherex T-55)
Ethylene oxide adducts of nonylphenol (Surfonic N-85, Surfonic N-95, Surfonic N-100)

| Surfactant Pairs | |
|---|---|
| Surfactant 1 (% concentration range) | Surfactant 2 (% concentrations) |
| Sorbitan monooleate (Span 80; 0.5–5.8) | Polyoxyethylene (20) sorbitan monooleate (Tween 80; 0.1–5.3) |
| Polyoxyethylene (2) oleyl ether (Brij 92; 0.5–6.0) | Polyoxyethylene (20) sorbitan monooleate (Tween 80; 0.1–5.3) |
| $C_9$–$C_{11}$ linear alcohol ethoxylate (Neodol 91-2.5; 0.5–6.0) | Polyoxyethylene (20) sorbitan monooleate (Tween 80; 0.1–5.3) |
| Block copolymer of propylene and ethylene oxide (Pluronic L-64; 0.3–5.8) | Sorbitan monooleate (Span 80; 0.1–5.2) |
| Fatty acid alkanolamide (Monamid 150 ADY; 0.5–6.5) | Octylphenoxy polyethoxyethanol (Triton X-35; 0.2–5.5) |
| Glyceryl laurate (Kessco 675; 0.3–5.8) | Sorbitan monooleate (Span 80; 0.1–5.2) |
| Linoleamide (Monamid B-442; 0.5–6.0) | Polyoxyethylene (20) sorbitan monooleate (Tween 80; 0.1–5.2) |

Preferred Primary Alcohols (% concentration range 0.1–3.1)

$CH_3$—$(CH_2)_{10}$—OH
Mixed $C_9$/$C_{10}$/$C_{11}$ alcohol (Neodol 91)
$C_{11}$ alcohol (Neodol 1)
$CH_3$—$(CH_2)_{11}$—OH
Mixed $C_{12}$/$C_{13}$ alcohol (Neodol 23)
$CH_3$—$(CH_2)_{13}$—OH
$CH_3$—$(CH_2)_{14}$—OH
Mixed $C_{14}$/$C_{15}$ alcohol (Neodol 45)
$CH_3$—$(CH_2)_{15}$—OH
$CH_3$—$(CH_2)_{16}$—OH
$CH_3$—$(CH_2)_{17}$—OH, Oleyl Preferred Polyhydroxy Alcohols and Polyhydroxy Alcohol Esters (% concentration range 0.1–6.0)

Glycerin, $C_3H_5(OH)_3$
Ethylene glycol, $CH_2OHCH_2OH$
1,2-Propylene glycol, $CH_3CHOHCH_2OH$
Diethylene glycol, $CH_2OHCH_2OCH_2CH_2OH$
Glycerol monolaurate, $C_{11}H_{23}COOCH_2CHOHCH_2OH$
Glycerol monooleate, $C_{17}H_{33}COOCH_2CHOHCH_2OH$
Glycerol monostearate, $(C_{17}H_{35})COOCH_2CHOHCH_2OH$ The following examples, all using possible combinations of the necessary components of the invention, are grouped according to their functional use. It should be understood that all variations may be used with the appropriate active ingredient to produce products with different functions and slightly different characteristics.

Air Freshener Emulsion and Aerosol Preparations

Example 1

1.6 grams of methylparaben (0.2% by weight) and 4.0 grams of ethanol (0.5%), were placed in a 2-liter stainless steel mixing beaker. The two were hand mixed with a spatula until the methylparaben was completely dissolved.

12 grams of Monamid 150 ADY (fatty acid alkanolamide) (1.5%), 8.0 grams of glycerol (1%), 0.8 grams of Neodol 1, (1-undecanol; 0.1%), and 2.4 grams of IFF fragrance 6673-AP (0.3%) were placed in the mixing container. The contents of the container were hand mixed with a spatula to produce a homogeneous mix.

699.2 grams of deionized water (87.4%) was next placed in the container. Agitation with a Gifford-Wood, Model 1L, homogenizer mixer was initiated and medium shear utilized to the point (5 minutes) of producing a homogeneous, thickened liquid, ringing gel. Lamellar layers were present in the batch at this point and continued to form as the batch stood for an additional couple of hours.

Lamellar or liquid crystal structure was indicated by polarized light microscopy, fluorescent probe analysis, and Frequency Response Analysis (FRA).

205.6 grams of the above lamellar system (91%) was placed in a 400 ml. beaker, which was then subjected to sonification for two minutes using a Sonics & Materials, Inc., 600 Watt High Intensity Ultrasonic Processor. Ultrasonic agitation converted the batch to a semi-clear emulsion solution with a viscosity similar to that of water, a pH of 8.4, and a specific gravity of 0.9909. Fluorescent probe analysis and FRA indicated the presence of vesicles.

Example 2

A formulation made up according to the procedure of Example 1 with 3% Monamid 150 ADY, 0.1% Neodol 1, 1% glycerol, and 0.3% fragrance was—before sonification—photographed by TEM as described before.

FIG. 1 (40,300 magnification) shows the multilamellar liposome structures present in the lamellar phase of this formulation.

Figure 2:
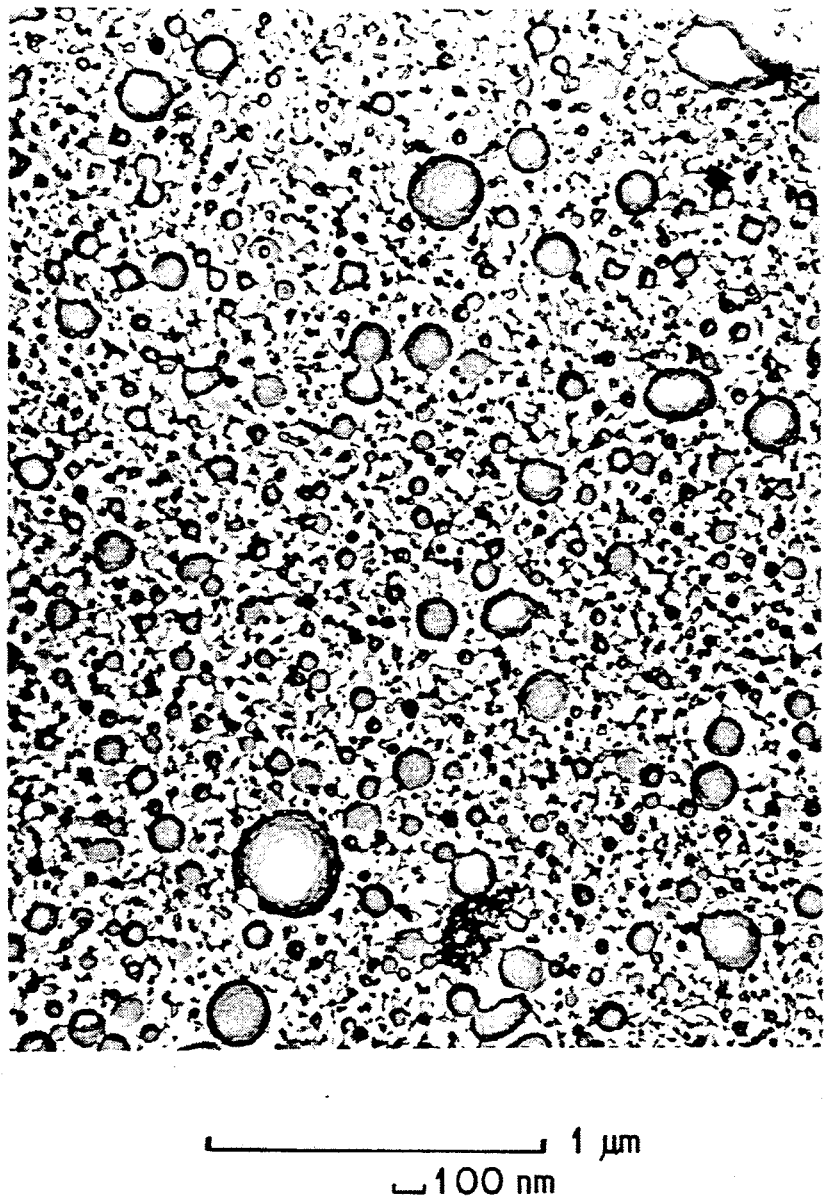

FIG. 2 (62,000 magnification), taken after sonification of the lamellar phase, shows the presence of many vesicular structures of an average size of 20–100 nm in the emulsion. Some larger unilamellar vesicles are also present.

Preparation of the pressurized air freshener containing aerosol container 205.6 grams (91%) of the intermediate described above was placed in a 305 cc. metal can, and a standard dip tube, push-activated vapor tap aerosol valve (Precision Valve Corp. Stem 0.024", vapor tap 0.013") was crimped on. The can was evacuated to 20 inches (50.8 cm) of vacuum. The can was then pressure filled with 36 ml. (20.2 grams, 9%) of a propellant blend consisting of 33% A-108 propane and 67% of A-17 butane. The aerosol can was held at 130° F. for 20 minutes in a hot tank, and the pressure was checked with a hand held pressure gauge (Liquid Filled, U.S. Gauge, 0–160 psi) and found to be 120 psi. The can was then cooled to 72° F. (22.2° C.). The finished product was found to have a pressure of 54 psi (3796.74 gr/sq. cm).

Example 3

A formulation made up according to the procedure of Example 1 but using 1.5% Monamid 150 ADY, 0.1% Neodol 1, 1% glycerol, 0.3% fragrance, 88.10% distilled water and 9% of the propane-butane blend produced a stable, semi-clear liquid phase aerosol system having a pressure of 56 psi (3937.36 gr/sq. cm), while increasing the Monamid level to 6.5% produced an aerosol system having a pressure of 55 psi (3867 gr/sq. cm). Increasing the level of glycerol to 6% produced a system with a pressure of 53 psi (3867 gr/sq. cm).

Example 4

A formulation made up according to the procedure of Example 1 but using 2% Monamid 150 ADY, 0.2% methylparaben, 0.5% ethanol, 1% glycerol, 0.3% fragrance, 90% deionized water, 3% n-pentane, and 3% propane produced an aerosol system with a pressure of 55 psi (3867 gr/sq. cm).

Example 5

A formulation similar to that of Example 3 but with 6% n-pentane and 3% propane (and 87% water) produced a system with a pressure of 37 psi (2601.47 gr/sq. cm), lower than the ideal pressure for aerosols intended to produce sprays but appropriate for aerosols intended to deliver such products as post-delivery foaming gels.

Example 6

As discussed before, the non-ionic surfactant of the aqueous component need not be of a single type. It can be a combination of two types of non-ionic surfactants that interact to produce the vesicular structure of the system.

A formulation made up according to the procedure of Example 1 but using 1.5% Span 80 (sorbitan monooleate), 0.3% Tween 80 (polyoxyethylene (2) oleyl ether), 0.25% Neodol 1, 1% glycerol, 0.3% fragrance, 88.35% distilled water, and 9% of the propane-butane blend produced an aerosol system having a pressure of 54 psi (3796.74 gr/sq. cm).

Example 7

A formulation made up according to the procedure of Example 1 but using 2.5% Monamid 150 ADY, 0.2% methylparaben, 0.1% Neodol 1, 1% ethylene glycol, 0.3% fragrance, 87.1% deionized water, and 9% of the propane-butane blend, produced an aerosol system with a pressure of 55 psi (3867. gr/sq. cm).

Example 8

A formulation made up according to the procedure of Example 1 but using 2.5% Monamid 150 ADY, 0.1% Neodol 1, 1% glycerol monooleate, 0.3% fragrance, 87.1% distilled water and 9% of the propane-butane blend produced a stable, semi-clear liquid phase aerosol system having a pressure of 53 psi (3726.43 gr/sq. cm).

Insecticide Emulsion and Aerosol Preparation

Example 9

1.6 grams of methylparaben (0.2%) and 4.0 grams of ethanol (0.5%) were placed in a 2-liter stainless steel mixing beaker. The two were hand mixed with a spatula until the methylparaben was completely dissolved.

16 grams of Monamid 150 ADY (2%), 12.0 grams of glycerol (1.5%), and 1.6 grams of 2,2,4-trimethyl pentane (0.2%) were next placed in the mixing container. The contents of the container were hand mixed with a spatula to produce a homogeneous mix.

668.8 grams of deionized water (83.6%) was next placed in the container. Agitation with a Gifford-Wood, Model 1L, Homogenizer mixer was initiated and medium shear utilized to the point (5 minutes) of producing a homogeneous, thickened liquid, ringing gel. Lamellar layers were present in the batch at this point and continued to form as the batch stood for an additional couple of hours.

Lamellar, liquid crystal structure was indicated by polarized light microscopy, fluorescent probe analysis, and FRA.

8 grams of pyrethrum extract (Aerosol grade 20% Pyrethrins) (3%) were placed in the container, and the gel was then sheared for 5 minutes to form a homogeneous, milky white, lamellar system.

207.4 grams (91%) of the above lamellar system was placed in a 400 ml. beaker, which was then subjected to sonification for two minutes using a Sonics & Materials, Inc., 600 Watt (2047.74 BTU/Hr.) High Intensity Ultrasonic Processor. Ultrasonication converted the batch to a milky white, emulsion solution with a viscosity similar to water, pH of 8.94, and a specific gravity of 1.0005. Fluorescent probe analysis and FRA indicated the presence of vesicles.

Preparation of the Pressurized Insecticide-Containing Aerosol Container 207.4 grams (91%) of the intermediate described above was placed in a 305 cc. metal can, and a vapor tap aerosol valve was crimped on. The can was evacuated to 20 inches of vacuum. The can was then pressure filled with 36 ml. (20.2 g, 9%) of a propellant blend consisting of 33% A-108 propane and 67% of A-17 butane. The aerosol can was held at 130° F. (54° C.) for 20 minutes in a hot tank, and the pressure was checked with a hand held pressure gauge (Liquid Filled, U.S. Gauge 0-160 psi) and found to be 122 psi (8577.82 gr/sq. cm). The can was then cooled to 72° F. (22.2° C.). The finished product was found to have a pressure of 55 psi (3867 gr/sq. cm).

Insect Repellent Emulsion and Aerosol Preparation

Example 10

20 grams of Monamid B-442 (linoleamide) (2.5%), 12.0 grams of glycerol (1.5%) and 2.4 grams of 2,2,4-trimethyl pentane (0.3%) were next placed in the mixing container. The contents of the container were hand mixed with a spatula to produce a homogeneous mix.

66.8 grams of deionized water (71.7%) was next placed in the container. Agitation with a Gifford-Wood, Model 1L, Homogenizer mixer was initiated and medium shear utilized to the point (5 minutes) of producing a homogeneous, thickened liquid, ringing gel. Lamellar layers were present in the batch at this point and continued to form as the batch stood for an additional couple of hours.

Liquid crystal structure was confirmed by polarized light microscopy, fluorescent probe analysis and FRA.

120 grams of DEET (15%) were placed in the container, and the gel was then sheared for 5 minutes to form a homogeneous, milky white, lamellar system.

728 grams of the above batch was placed in a 400 ml. beaker, which was then subjected to sonification for two minutes using a Sonics & Materials, Inc., 600 Watt High Intensity Ultrasonic Processor. Ultrasonication converted the batch to a milky white, vesicular solution with a viscosity similar to water, pH of 8.94, and a specific gravity of 1.0005. Fluorescent probe analysis and FRA indicated the presence of vesicles.

Preparation of the Pressurized Insect Repellent-Containing Aerosol Container 728 grams of the intermediate described above was placed in a 305 cc. metal can, and a vapor tap aerosol valve was crimped on. The can was evacuated to 20 inches (50.8 cm) of vacuum. The can was then pressure filled with 36 ml. of a propellant blend consisting of 33% A-108 propane and 67% of A-17 butane. The aerosol can was held at 130° F. (54° C.) for 20 minutes in a hot tank, and the pressure was checked with a hand held pressure gauge (Liquid Filled, U.S. Gauge 0-160 psi) and found to be 122 psi (8577.82 gr/sq. cm). The can was then cooled to 72° F. (22.2° C.). The finished product was found to have a pressure of 55 psi (3867 gr/sq. cm).

Dye-Containing Emulsion Preparation

Example 11

A formulation was made up according to the procedure of Example 8 but using 2.5% Monamid 150 ADY, 0.1% Neodol 1, 1.0% glycerol, 0.3% 2,2,4-trimethyl pentane, and 0.02% 5(6) carboxy fluorescein. Capture volumes (CV, defined as the captured volume per gram of surfactant, the surfactant in this case being considered as including both the primary alcohol and the other surfactants) were determined using a dialysis technique (using the carboxy fluorescein as the tracer). The results were: CV for the liquid crystal system, 1.9 ml/g; CV for the vesicle system, 18.9 ml/g. Thus, the vesicular system is able to entrap and hold a large volume of active organic ingredient.

Figure 3:
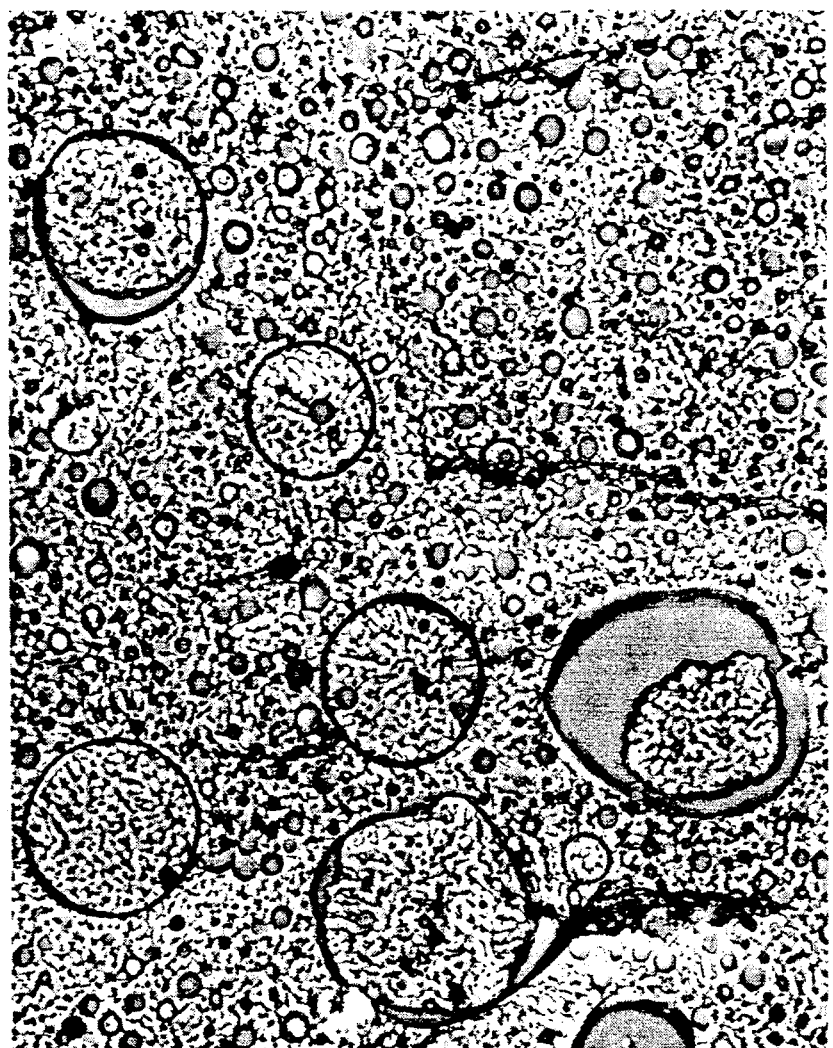

FIG. 3, (46,500 magnification) shows this preparation after sonification. The vesicular structures visible range from 25 to 300 nm, with most in the 20 to 100 nm range.

Emulsion Cologne Preparation

Example 12

A formulation was made up according to the procedure of Example 1 with 3.0% tallow monoethanolamide 5.5 mole ethoxylate (Sherex Varamid T55), 0.2% dimethicone, 1.5% glycerin, 2.0% fragrance, 0.5% Aerosurf TA-100 (distearyl dimethyl ammonium chloride), 0.0001% dye, 1.0% ethanol, 0.005% silicon antifoam emulsion (Dow Corning DB-110) and 92.3% deionized water. When fragrance was applied to a user's skin in an ethanol control mixture and in the vesicular preparation, the odor of the fragrance in the vesicular preparation remained strong longer than it did in the control mixture (tested at 3 hours after application).

It would appear that, in the same way that the vesicular structures reservoir and gradually release propellant in an aerosol preparation, they also reservoir and gradually release other active ingredients.

Stain Removing Emulsion Preparation

Example 13

A formulation was made up according to the procedure of Example 1 with 7.7% $C_{12}$–$C_{13}$ linear primary alcohol ethoxylate (surfonic L24-4). 5% of 50% citric acid 3.5% of 50% NaOH, 0.05% silicon antifoam emulsion (Dow Corning DB-110), 0.5% propylene glycol in butyl ether (Dowanol PnB), 0.7% distearyl dimethyl ammonium chloride, 0.9% glycerin, 2.1% tallow mono-ethanolamide 5.5 mole ethoxylate (Sherex Varamide T55), 0.2% Neodol 1, 0.1% Barquat 4250 (alkyl dimethyl benzyl ammonium chloride/alkyl dimethyl ethyl benzyl ammonium chloride), 0.05% Tinopal CBS-X (distrylbiphenyl derivative), and 80.9% deionized water.

The resulting vesicular preparation when compared to two commercially available stain removal products, showed improved stain/soil removal properties with almost all types of stain or soil. The vesicular preparation is most noticeably superior to currently available products in the area of oily stains.

Skin Care Emulsion Preparation

Example 14

A formulation was made up according to the procedure of Example 1 with 12% glycerin, 5% distearyl dimethyl ammonium chloride (Arosurf TA-103), 4% petrolatum, 3% isopropyl palmitate, 2.5% cetyl alcohol, 1.25% dimethicone, 0.1% methyl paraben, 0.05% fragrance, 0.04% propyl paraben, and 0.01% sodium chloride, the balance being deionized water.

The resulting vesicular preparation, when compared to a standard emulsion-type skin lotion showed an improved cosmetic feel on the user's skin being neither greasy nor tacky while imparting a feel of softness to the skin.

Insect Repellent Preparation

Example 15

The fact that the vesicular formulation of the present invention proved to provide a "reservoiring effect" for propellants has been discussed, as has a similar effect with fragrances. It was found that when the active ingredient added to the vesicle preparation was an insect repellent (DEET), the resulting preparation showed a more lasting repellency effect than did a preparation of DEET in ethanol. It would appear that the vesicles provide a similar reservoiring effect for the DEET molecules, and that a vesicular DEET preparation prevents rapid evaporation of DEET from a user's skin and provides longer duration protection.

A formulation was made up according to the procedure of

Example 1 with the following components: 15.0% DEET, 0.2% methylparasept, 0.5% ethanol, 2.8% Monamid B-442, 1.5% glycerine, 0.3% 2,2,4-Trimethyl Pentane, and 79.7% deionized water.

This preparation was tested against 1) formulations of DEET in ethanol (14.25% DEET, 0.75% DEET isomers, 85% ethanol) and 2) an aerosol formulation of DEET (14.25% DEET, 0.75% DEET isomers, 10% propellant, 75% ethanol). In all cases, the vesicular DEET preparation provided longer lasting protection against bites from either mosquitoes or stable flies.

Two sets of tests were conducted to determine the relative protection times of this vesicular DEET formulation. Following are the summarized data for each test. Tables 1 and 2 show the results of the vesicular DEET formation when compared to a liquid control; Tables 3 and 4 show the results when an aerosol preparation was used as the control. Included in the summary for each test is a table of the mean protection times, and a table with the Standard Errors of the Means (SEM). FIG. 4 shows a bar graph for the results of Test 1 and FIG. 5 shows a bar graph for the results of Test 2.

TABLE 1

Protection Times of Vesicular DEET vs. DEET solution on mosquitoes (M) and stable flies (SF).

| | DEET mg/cm$^2$ | No. Reps | Mean Protection Time (in Hours)[1] | | | |
|---|---|---|---|---|---|---|
| | | | Lands | | Bites | |
| | | | M | SF | M | SF |
| Vesicular DEET | 0.23 | 4 | 0.38a | 1.00a | 4.38a | 3.88a |
| DEET (in EtOH) | 0.23 | 4 | 1.25a | 0.75a | 2.25b | 2.25b |

[1] Numbers in columns followed by the same letters are not significantly different (T-Test, $\alpha = 0.10$).

TABLE 2

Standard Errors of the Means (SEM) for Table 1.

| | SEMs for Mean Protection Time | | | |
|---|---|---|---|---|
| | Lands | | Bites | |
| Formulation | M | SF | M | SF |
| Vesicular DEET | 0.24 | 0.54 | 0.63 | 0.63 |
| DEET (in EtOH) | 0.52 | 0.32 | 0.78 | 0.32 |

TABLE 3

Protection Times of Vesicular DEET vs. DEET aerosol on mosquitoes (M) and stable flies (SF).

| | DEET mg/cm$^2$ | No. Reps | Mean Protection Time (in Hours)[1] | | | |
|---|---|---|---|---|---|---|
| | | | Lands | | Bites | |
| | | | M | SF | M | SF |
| Vesicular DEET | 0.23 | 6 | 0.00b | 1.83a | 4.00a | 5.67a |
| DEET (in EtOH with propellant) | 0.23 | 6 | 0.25a | 0.50b | 1.58b | 2.08b |

[1] Numbers in columns followed by the same letters are not significantly different (T-Test, $\alpha = 0.10$).

TABLE 4

Standard Errors of the Means (SEM) for Table 3.

| | SEMs for Mean Protection Time | | | |
|---|---|---|---|---|
| | Lands | | Bites | |
| Formulation | M | SF | M | SF |
| Vesicular DEET | 0.00 | 0.62 | 0.98 | 0.38 |
| DEET (in EtOH with propellant) | 0.17 | 0.26 | 0.24 | 0.44 |

A different formulation, using 0.25% Neodol 1 instead of the ethanol (% water adjusted accordingly), was also made up and had similar effectiveness and properties to the formulation tested.

Other modifications of the aqueous emulsion preparation and of the aerosol delivery system utilizing that preparation of the present invention will become apparent to those skilled in the art from an examination of the above patent Specification and drawings. Therefore, other variations of the present invention may be made which fall within the scope of the following claims even though such variations were not specifically discussed above.

Industrial Applicability

Both the aqueous emulsion preparation and the aerosol delivery system of the present invention can be used to deliver many types of products. Active ingredients to be delivered by such systems can include such things as pesticides, insect repellents, fragrances, emollients, polymers, and polishing or cleansing compounds, etc.

What I claim is:

1. An aqueous emulsion system comprising a mixture of a non-ionic surfactant, a $C_2$-$C_{18}$ primary alcohol, a compound selected from the group consisting of polyhydroxy alcohols, polyhydroxy alcohol esters and mixtures thereof, and active ingredient and water, this mixture being processed so as to produce an aqueous emulsion system containing vesicular structures of an average size of 10–300 nm.

2. The aqueous emulsion system of claim 1 wherein the mixture comprises a non-ionic surfactant, a $C_9$-$C_{18}$ primary alcohol, a compound selected from the group consisting of a $C_2$-$C_6$ polyhydroxy alcohol, a $C_{10}$-$C_{30}$ polyhydroxy alcohol ester and mixtures thereof, an active ingredient and water.

3. The aqueous emulsion system of claim 1 wherein the mixture comprises 0.25% to 6.5% of a non-ionic surfactant, 0.001% to 3.5% of a $C_9$-$C_{18}$ primary alcohol, 0.1% to 6% of a $C_2$-$C_6$ polyhydroxy alcohol, and 0.01% to 20% of an organic active ingredient, the balance of the emulsion system being water.

4. The aqueous emulsion system of claim 1 wherein the non-ionic surfactant is a mixture of two or more non-ionic surfactants.

5. The aqueous emulsion system of claim 1 wherein the non-ionic surfactant is a non-ionic surfactant having a pair of hydrocarbon chains attached to its functional group.

6. The aqueous emulsion system of claim 1 wherein the non-ionic surfactant is a non-ionic surfactant having a hydrocarbon chain attached to its functional group.

7. The aqueous emulsion system of claim 1 wherein the non-ionic surfactant is selected from the group consisting of an ethylene oxide adduct of nonyl phenol, a fatty acid alkanolamide, and an ethoxylated amine.

8. The aqueous emulsion system of claim 1 wherein the primary alcohol is selected from the group consisting of a $C_{10}$ alcohol or a $C_{11}$ alcohol.

9. The aqueous emulsion system of claim 1 additionally comprising from 0.1% to 0.5% of a preservative.

10. The aqueous emulsion system of claim 1 wherein the mixture comprises 0.25% to 6.5% of a fatty acid alkanolamide surfactant, 0.001% to 3.5% of a $C_{11}$ primary alcohol, 0.1% to 6% of glycerol and 0.01% to 20% of an organic active ingredient, the balance of the emulsion being water.

11. The aqueous emulsion system of claim 10 wherein the organic active ingredient is an insect repellent.

12. The aqueous emulsion system of claim 10 wherein the organic active ingredient is an odor-imparting material.

13. The aqueous emulsion system of claim 10 wherein the organic active ingredient is a cleaning and polishing material.

14. The aqueous emulsion system of claim 10 wherein the organic active ingredient is a dermal treatment material.

15. The aqueous emulsion system of claim 10 wherein the organic active ingredient is a stain removal agent.

16. A method of preparing an aqueous emulsion system containing vesicular structures of an average size of 10–300 nm comprising:

placing into a container a non-ionic surfactant, a $C_2$-$C_{18}$ primary alcohol, a compound selected from the group consisting of polyhydroxy alcohols, polyhydroxy alcohol esters and mixtures thereof, and an organic active ingredient, mixing these ingredients in the container to produce a homogeneous mixture, adding water to the container, further mixing the ingredients in the container to form a lamellar stage, and adding energy, by means of utilizing a method selected from the group consisting of a high energy shearing and sonification, to the lamellar stage to produce the vesicle containing emulsion.

17. The method of preparing an aqueous emulsion system of claim 15 wherein the method comprises:
    placing into a container a non-ionic surfactant,
    a $C_9$-$C_{18}$ primary alcohol,
    a compound selected from the group consisting of a $C_2$-$C_6$ polyhydroxy alcohol, a $C_{10}$-$C_{30}$ polyhydroxy alcohol ester and mixtures thereof, and
    an organic active ingredient,
    mixing these ingredients in the container to produce a homogeneous mixture,
    adding water to the container,
    further mixing the ingredients in the container to form the lamellar stage, and
    adding energy, by means of utilizing a method selected from the group consisting of a high energy shearing or sonification, to the lamellar stage to produce the vesicle containing emulsion.

18. The method of preparing an aqueous emulsion system of claim 15 wherein the method comprises:
    placing into a container from 0.25 to 6.5% by weight of a non-ionic surfactant,
    from 0.001% to 3.5% by weight of a $C_9$-$C_{18}$ primary alcohol,
    from 0.1% to 6% of a $C_2$-$C_6$ polyhydroxy alcohol, and
    from 0.01% to 20% of an organic active ingredient,
    mixing these ingredients in the container to produce a homogeneous mixture,
    adding water to the container to bring the total weight to 100%,
    further mixing the ingredients in the container to form the lamellar stage, and
    adding energy, by means of utilizing a method selected from the group consisting of a high energy shearing or sonification, to the lamellar stage to produce the vesicle containing emulsion.

19. The method of preparing an aqueous emulsion system of claim 15 wherein the non-ionic surfactant is a mixture of two or more non-ionic surfactants.

20. The method of preparing an aqueous emulsion system of claim 15 wherein the non-ionic surfactant is a non-ionic surfactant having a pair of hydrocarbon chains attached to its functional group.

21. The method of preparing an aqueous emulsion system of claim 15 wherein the non-ionic surfactant is a non-ionic surfactant having a hydrocarbon chain attached to its functional group.

22. The method of preparing an aqueous emulsion system of claim 15 wherein the non-ionic surfactant is a mixture of a non-ionic surfactant having a pair of hydrocarbon chains attached to its functional group and a non-ionic surfactant having a hydrocarbon chain attached to its functional group.

23. The method of preparing an aqueous emulsion system of claim 15 wherein the non-ionic surfactant is selected from the group consisting of an ethylene oxide adduct of nonyl phenol, a fatty acid alkanolamide, and an ethoxylated amine.

24. The method of preparing an aqueous emulsion system of claim 15 wherein the primary alcohol is selected from the group consisting of a $C_{10}$ alcohol or a $C_{11}$ alcohol.

25. The method of preparing an aqueous emulsion system of claim 15 wherein the aqueous emulsion additionally comprises from 0.1% to 0.5% of a preservative.

26. A method of preparing an aqueous emulsion system containing vesicular structures of an average size of 10–300 nm comprising:
    preparing a lamellar phase system by:
    placing into a container from 0.25 to 6.5% by weight of a fatty acid alkanolamide surfactant,
    from 0.001% to 3.5% by weight of a $C_{11}$ primary alcohol,
    from 0.1% to 6% of glycerol, and
    from 0.01% to 20% of an organic active ingredient,
    mixing these ingredients in the container to produce a homogeneous mixture,
    adding water to the container to bring the total weight to 100%,
    further mixing the ingredients in the container to form a lamellar stage, and
    adding energy, by means of utilizing a method selected from the group consisting of a high energy shearing or sonification, to the lamellar stage to produce the vesicle containing emulsion.

27. The method of preparing an aqueous emulsion system of claim 15 wherein the organic active ingredient is an insect repellent material.

28. The method of preparing an aqueous emulsion system of claim 15 wherein the organic active ingredient is an odor imparting material.

29. The method of preparing an aqueous emulsion system of claim 15 wherein the organic active ingredient is a cleaning and polishing material.

30. The method of preparing an aqueous emulsion system of claim 15 wherein the organic active ingredient is a dermal treatment material.

31. The method of preparing an aqueous emulsion system of claim 15 wherein the organic active ingredient is a stain removal agent.

* * * * *